United States Patent [19]

Canada

[11] 4,366,155
[45] Dec. 28, 1982

[54] 1-BENZOYL-3-(6-OXOPYRIDAZINYL-)UREAS, COMPOSITIONS, AND INSECTICIDAL METHOD

[75] Inventor: Emily J. Canada, Indianapolis, Ind.

[73] Assignee: Eli Lilly and Company, Indianapolis, Ind.

[21] Appl. No.: 249,054

[22] Filed: Mar. 30, 1981

[51] Int. Cl.³ .................... C07D 237/22; A01N 43/58
[52] U.S. Cl. ..................................... 424/250; 544/239
[58] Field of Search ......................... 424/250; 544/239

[56] References Cited

U.S. PATENT DOCUMENTS

| | | | |
|---|---|---|---|
| 3,748,356 | 7/1973 | Wellinga et al. | 260/553 E |
| 3,947,437 | 3/1976 | Johnston | 544/239 |
| 4,083,977 | 4/1978 | Miesel | 424/250 |
| 4,092,421 | 5/1978 | Wade | 424/266 |
| 4,133,956 | 1/1979 | Abdulla | 544/353 |
| 4,160,834 | 7/1979 | Miesel | 424/250 |
| 4,173,639 | 11/1979 | Suhr | 424/263 |
| 4,212,870 | 7/1980 | Gibbs | 424/263 |

FOREIGN PATENT DOCUMENTS

| | | |
|---|---|---|
| 124918 | 3/1977 | Fed. Rep. of Germany. |
| 2748636 | 5/1978 | Fed. Rep. of Germany. |
| 131172 | 6/1978 | Fed. Rep. of Germany. |
| 42-9592 | 5/1967 | Japan. |
| 2026476 | 6/1978 | United Kingdom. |

OTHER PUBLICATIONS

C & E News, Final Program, 1977 ACS Meeting, pp. 24 & 57, Jul. issue, Talk No. 73, DeMilo et al.
Abstracts of Papers, 174th ACS Meeting, 1977 Abstract of Talk No. 73, DeMilo et al.
DeMilo et al., J. Agr. Food Chem. 26, 164 (1978), Presented orally at 174th ACS Meeting, 1977.
Wellinga et al., J. Agr. Food Chem. 21, 348 (1973).
Wellinga et al., J. agr. Food Chem. 21, 993 (1973).
Hajjar et al., Science, 200, 1499 (1978).
Zupan et al. Chem. Abs. 77, 13992h (1972), (See Attached Index Entry page).
Kaisha, Chem. Abs. 94, 208901t (1981).

*Primary Examiner*—Mark L. Berch
*Attorney, Agent, or Firm*—Charles W. Ashbrook; Arthur R. Whale

[57] ABSTRACT

Insecticidal agents characterized as 1-(benzoyl)-3-(6-oxopyridazinyl)urea are provided. Agricultural compositions and an insecticidal method are disclosed.

25 Claims, No Drawings

1-BENZOYL-3-(6-OXOPYRIDAZINYL)UREAS, COMPOSITIONS, AND INSECTICIDAL METHOD

BACKGROUND OF THE INVENTION (a) Field of the Invention

This invention relates to novel 1-benzoyl-3-(6-oxopyridazinyl)ureas, insecticidal compositions containing these compounds and methods of controlling insects employing these compounds.

(b) Discussion of the Prior Art

The prior art discloses various substituted benzoyl ureas. For example, numerous substituted benzoyl ureas are disclosed in U.S. Pat. No. 3,748,356 (Wellinga et al.) and are said to be insecticidal. Most of the benzoyl ureas disclosed in *Wellinga et al.* are substituted benzoyl phenyl ureas. A few substituted benzoyl pyridyl ureas are also disclosed. Other substituted benzoyl phenyl ureas are disclosed in *Journal of Agriculture and Food Chemistry*, Vol. 21, No. 3 (1973) and Vol. 21, No. 6 (1973).

In addition to the benzoyl pyridyl ureas mentioned by Wellinga et al., other benzoyl ureas substituted at the 3-position with a heterocyclic nitrogen-containing moiety are disclosed in the art. For example, in U.S. Pat. No. 4,083,977 (Miesel), certain 1-(substituted benzoyl)-3-(substituted pyrazinyl)ureas are disclosed and are said to be useful as insecticides. Certain substituted benzoyl pyridinyl ureas useful as insecticides are disclosed by Suhr in U.S. Pat. No. 4,173,639. Several heterocyclic benzoyl urea compounds are listed in *Journal of Agriculture and Food Chemistry*, Vol. 26, No. 1 (1978). The compounds mentioned in this article are 1-(2,6-difluorobenzoyl)-3-(heterocyclic)-ureas. Hetrocyclic groups listed include: 3,4-dimethyl-5-isoxazolyl, 5-(1-methylethyl)-1,3,4-thiadiazol-2-yl, 5-chloro-2-pyridinyl, 4-chloro-6-methyl-2-pyrimidinyl, and 4,6-dimethoxy-1,3,5-triazin-2-yl.

The compounds of this invention differ from those of the art in that a 6-oxopyridazinyl group is required on one of the urea nitrogen atoms.

SUMMARY OF THE INVENTION

This invention provides 1-(substituted benzoyl)-3-(6-oxopyridazinyl)ureas of the formula:

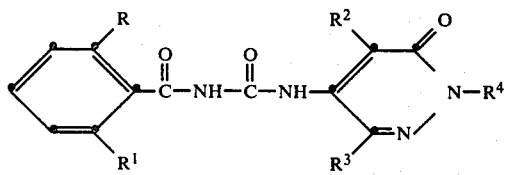

wherein R is chloro, fluoro or bromo, $R^1$ is hydrogen, chloro, fluoro or bromo, $R^2$ and $R^3$ are independently hydrogen, chloro or bromo, and $R^4$ is selected from the group consisting of branched alkyl, cycloalkyl, 4-chlorophenyl, 3,5-dichlorophenyl, 4-bromophenyl, 3-trifluoromethylphenyl 3,5-bis(trifluoromethyl)phenyl, 4-chlorobenzyl and 4-methoxyphenyl, with the provisos that when R is fluoro, $R^1$ is other than hydrogen; that one of $R^2$ and $R^3$ is hydrogen; that $R^4$ is other than 3-trifluoromethylphenyl when R is bromo and $R^2$ and $R^3$ are hydrogen or when R and $R^3$ both are chloro and $R^1$ is hydrogen; and that $R^4$ is 4-methoxyphenyl only when R and $R^1$ both are chloro and $R^2$ is hydrogen or chloro.

The compounds provided herein possess insecticidal activity. The invention also comprises insecticidal compositions comprising the compounds of the above formula admixed with a suitable inert carrier. Also provided is a method of controlling insects employing the compounds defined above.

DETAILED DESCRIPTION OF THE INVENTION

The compounds of this invention can be prepared by methods familiar to those skilled in the art of organic synthesis. A preferred method involves reaction of approximately equal weight quantities of a substituted benzoyl isocyanate with a 4-amino-1,6-dihydro-6-oxopyridazine (also referred to as a 4-amino-6-pyridazinone). The general reaction can be represented as follows:

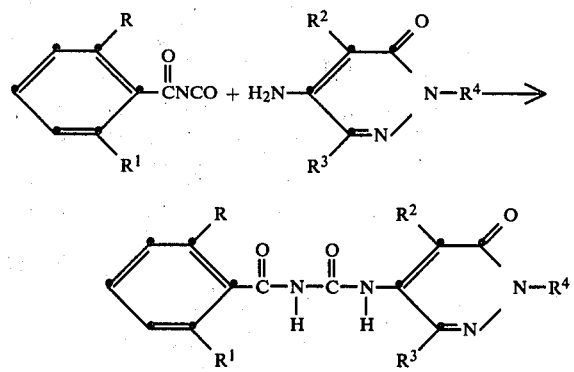

where R, $R^1$, $R^2$, $R^3$ and $R^4$ are as defined above.

In the above definition of $R^4$, "branched alkyl" refers to groups containing from 3 to 7 carbon atoms, for example isopropyl, isobutyl, tertiary butyl (t-butyl), isopentyl, neopentyl, isohexyl, neohexyl, 2-methylhexyl, isoheptyl and related groups. The term "cycloalkyl" as used herein refers to cycloalkyl groups containing from 3 to 7 carbon atoms. Typical cycloalkyl groups include cyclopropyl, cyclobutyl, cyclopentyl, cyclohexyl and cycloheptyl.

The 2-substituted or 2,6-disubstituted benzoyl isocyanates which are starting materials in the above scheme are in general known compounds and can be prepared by known methods. For example, the desired benzoyl isocyanate can be obtained by reacting the corresponding benzamide with oxalyl chloride in the presence of a solvent following the procedure described in *Journal of Organic Chemistry*, Vol. 27 (1962) at page 3742 (Speziale et al.). The reaction is generally conducted at an elevated temperature of about 50° to about 100° C., preferably at the boiling point of the solvent used. Solvents which can be used include aromatic hydrocarbons such as benzene, toluene, xylene, as well as chlorinated hydrocarbons such as methylene chloride, chloroform, carbon tetrachloride, dichloroethane and the like.

Typical 2-substituted and 2,6-disubstituted benzoyl isocyanates which can be employed in the synthesis of compounds of this invention include 2-chlorobenzoyl isocyanate, 2-bromobenzoyl isocyanate, 2-fluoro-6-bromobenzoyl isocyanate, 2-bromo-6-chlorobenzoyl isocyanate, 2,6-dibromobenzoyl isocyanate, and 2,6-difluorobenzoyl isocyanate.

The preparation of the 4-amino-6-pyridazinones which are useful as starting materials according to the above general scheme is described in *Angew. Chem., International Edition*, Vol. 4 No. 4 (1965) at pages 292–300 (Drury). The pyridazinone compounds wherein $R^2$ is chloro or bromo are prepared by reacting a substituted hydrazine with a 2,3-dihalo-3-formylacrylic acid (specific acids of this type are referred to herein by their common names, e.g. mucochloric or mucobromic acid) to produce the corresponding 4,5-dihalopyridazinone. Reaction of this product with ammonia yields the desired 4-amino-5-(chloro or bromo)-pyridazinone.

The pyridazinones which are substituted at the 3-position with chloro or bromo (i.e. $R^3$ is chloro or bromo) are prepared by reacting an appropriately substituted hydrazine with bromomaleic anhydride to yield the corresponding 3-hydroxy-4-bromo-6-pyridazinone. Chlorination or bromination results in the 3-chloro-4-bromo derivative or the 3,4-dibromo derivative. Subsequent reaction with ammonia produces the 3-chloro (or bromo)-4-amino compound which is then used to prepare the insecticidal 1-benzoyl-3-(6-oxopyridazinyl)ureas of this invention.

The unsubstituted pyridazinone intermediates wherein $R^2$ and $R^3$ both are hydrogen can be prepared by hydrogenating the 4-amino-5-halo derivative to the 4-amino compound which is then reacted with a benzoyl isocyanate to form the urea compounds of the invention.

Illustrative of the 4-amino-6-pyridazinones which can be employed in the preparation of the compounds of this invention include the following:
1-isopropyl-4-amino-1,6-dihydro-6-oxopyridazine;
1-t-butyl-4-amino-5-bromo-1,6-dihydro-6-oxopyridazine;
1-cyclopropyl-4-amino-5-chloro-1,6-dihydro-6-oxopyridazine;
1-cycloheptyl-3-bromo-4-amino-1,6-dihydro-6-oxopyridazine;
1-(4-chlorophenyl)-3-chloro-4-amino-1,6-dihydro-6-oxopyridazine;
1-(3,5-dichlorophenyl)-4-amino-1,6-dihydro-6-oxopyridazine;
1-(4-bromophenyl)-4-amino-1,6-dihydro-6-oxopyridazine;
1-(3-trifluoromethylphenyl)-3-bromo-4-amino-1,6-dihydro-6-oxopyridazine;
1-[3,5-bis(trifluoromethyl)phenyl]-4-amino-5-chloro-1,6-dihydro-6-oxopyridazine;
1-(4-chlorobenzyl)-4-amino-1,6-dihydro-6-oxopyridazine;
1-(4-methoxyphenyl)-3-chloro-4-amino-1,6-dihydro-6-oxopyridazine; and
1-(4-chlorophenyl)-3-bromo-4-amino-1,6-dihydro-6-oxopyridazine.

According to the above general scheme, a benzoyl isocyanate is reacted with about an equal weight amount of a 4-amino-1,6-dihydro-6-oxopyridazine. The reaction typically is carried out in an inert solvent such as dichloromethane, acetonitrile, benzene, toluene or the like, and normally at a temperature of about 0° to about 100° C. The reaction routinely is conducted at about 20° to about 30° C., and is generally substantially complete after about ten to about twenty-four hours. Longer reaction times can be employed if desired. The product of the reaction, a 1-benzoyl-3-(6-oxopyridazinyl)urea of the invention, is isolated by filtration in the case of a precipitate, or by simply removing the reaction solvent, for instance by evaporation under reduced pressure, when the product does not precipitate. The product is readily purified by standard procedures, including crystallization from solvents such as ethanol, acetone, ethyl acetate and the like.

The 1-benzoyl-3-(6-oxopyridazinyl)ureas provided by this invention can be prepared by an alternative process which also employs the 4-amino-1,6-dihydro-6-oxopyridazine intermediates which are described above. Abdulla, in U.S. Pat. No. 4,133,956, describes a process for preparing benzoylureas which involves reacting a benzamide with phenyl chloroformate and an amine in the presence of an alkyl lithium compound such as methyl lithium or butyl lithium. The reaction is carried out by treating the benzamide with the alkyllithium and phenyl chloroformate to form an intermediate urethane, and then treating the urethane with the appropriate amine. Alternatively, the process is conducted by treating the benzamide with the alkyllithium to form the lithium salt, and then treating this salt with a carbamate formed from the appropriate amine and a phenyl chloroformate. To prepare the novel benzoyl urea compounds of this invention the amine used would be a suitable 4-amino-6-pyridazinone.

Preferred 1-benzoyl-3-(6-oxopyridazinyl)urea compounds of this invention are defined by the above formula wherein $R^2$ is chlorine or bromine, $R^3$ is hydrogen and R, $R^1$ and $R^4$ are as defined above. Also preferred are compounds of the above formula in which $R^4$ is t-butyl, 4-chlorophenyl, 4-bromophenyl, 3,5-dichlorophenyl, 3-trifluoromethylphenyl or 3,5-bis(trifluoromethyl)phenyl, and in particular those compounds in which $R^4$ is 3-trifluoromethylphenyl or 3,5-bis(trifluoromethyl)phenyl. Another preferred group of compounds are those in which R is chlorine, $R^1$ is hydrogen or chlorine, $R^2$ is chlorine or bromine and $R^3$ is hydrogen. Particularly preferred compounds of this group are those in which $R^4$ is 3-trifluoromethylphenyl or 3,5-bis(trifluoromethyl)phenyl.

Additional compounds which are preferred are those in which R is chlorine or fluorine, $R^1$ is hydrogen, chlorine or fluorine, $R^2$ is chlorine, $R^3$ is hydrogen and $R^4$ is t-butyl, provided that when R is fluorine, $R^1$ is chlorine or fluorine. Other compounds of interest are those compounds in which each of R and $R^1$ is chlorine, one of $R^2$ and $R^3$ is hydrogen and the other is chlorine, and $R^4$ is 4-methoxyphenyl.

Also of particular interest are compounds in which at least one of $R^2$ and $R^3$ is chlorine or bromine and especially compounds in which $R^2$ is chlorine while $R^3$ is hydrogen. As discussed above, benzoyl ureas substituted with certain heterocyclic nitrogen containing moieties are disclosed in the art to be insecticidal. In each case, the heterocyclic moiety is unsubstituted in the position ortho to the urea moiety. In contrast to this, the pyridazinone urea compounds of this invention can, and preferably are, substituted in the ortho position.

The following examples illustrate the preparation of typical compounds of this invention. Other compounds within the scope of the invention can be prepared by analogous methods, as will be readily apparent to those skilled in the art. In each example, the benzoyl pyridazinone urea compound is prepared by reacting a 2-substituted or 2,6-disubstituted benzoyl isocyanate with an appropriate 4-amino-6-pyridazinone. The preparation of typical 4-amino-6-pyridazinone compounds is also illustrated in the following examples.

As already noted, the 2- or 2,6-substituted benzoyl isocyanates are known compounds. They can be prepared by reacting a substituted benzoyl amide with oxalyl chloride. Illustrative of this process is the following description of the preparation 2,6-dichlorobenzoyl isocyanate.

PREPARATION 1

A solution was prepared by dissolving 47.5 grams of 2,6-dichlorobenzamide (commercially available) in 150 ml. of methylene dichloride. To this solution, 28 ml. of oxalyl chloride were added slowly over twenty minutes. The mixture was heated at reflux overnight. The reaction mixture was cooled and filtered and the filtrate was concentrated by evaporation of the solvent under reduced pressure. The oily residue was distilled to yield a product having a boiling point of about 69°–72° C. at 0.25 mm. The product, which weighed 20 grams, was identified as 2,6-dichlorobenzoyl isocyanate. Other 2- and 2,6-substituted benzoyl isocyanates can be similarly produced.

EXAMPLE 1

This example illustrates the preparation of 1-(2-chlorobenzoyl)-3-[1-(3,5-bis(trifluoromethyl)phenyl)-5-chloro-1,6-dihydro-6-oxopyridazin-4-yl]urea.

To a solution of 28.1 grams (0.166 mol.) of mucochloric acid dissolved in 120 milliliters of ethanol were added 37 grams (0.151 mol.) of 3,5-bis-(trifluoromethyl)phenylhydrazine. The mixture was stirred for about one hour, and then the ethanol was removed from the solution by evaporation under reduced pressure. Eighty milliliters of glacial acetic acid and 80 milliliters of acetic anhydride were added to the residue in one portion. The mixture was heated to reflux for four hours, and then cooled and the solvent was removed by evaporation under reduced pressure. Recrystallization of the residue from ethanol produced 51.7 grams of 4,5-dichloro-1-[3,5-bis(trifluoromethyl)-phenyl]-1,6-dihydro-6-oxopyridazine.

A solution of 9.75 grams of the 6-pyridazinone and 13.8 milliliters of concentrated ammonium hydroxide in 66 milliliters of dimethyl sulfoxide was placed in a sealed tube and heated at 100° C. for eight hours. Water was then added to the mixture causing a yellow precipitate to form. The precipitate was removed from the reaction mixture by filtration. The precipitate was washed with water and then recrystallized from ethanol. A yield of 6.1 grams of solid product having a melting point of 255°–262° C. was obtained. NMR confirmed the product to be 4-amino-5-chloro-1-[3,5-bis(trifluoromethyl)phenyl]-1,6-dihydro-6-oxopyridazine.

To produce the desired final product, 0.7 grams of the 4-amino pyridazine prepared above was partially dissolved in 15 milliliters of 1,2-dichloroethane and treated with 0.7 grams of 2-chlorobenzoyl isocyanate under a nitrogen atmosphere. The reaction mixture was stirred for about 16 hours at room temperature. The solvent was removed by evaporation and the residue was recrystallized from ethanol. A yield of 0.56 grams of solid product having a melting point of 187°–194° C. was obtained. A nuclear magnetic resonance spectrum confirmed the structure of the product to be 1-(2-chlorobenzoyl)-3-[1-(3,5-bis(trifluoromethyl)-phenyl)-5-chloro-1,6-dihydro-6-oxopyridazin-4-yl]urea.

Elemental analysis of the product gave the following results:

Calc. for $C_{20}H_{10}Cl_2F_6N_4O_3$ (Percent)—Theory: C, 44.55; H, 1.87; N, 10.39. Found: C, 44.32; H, 1.89; N, 10.50.

EXAMPLE 2

This example illustrates the synthesis of 1-(2-bromobenzoyl)-3-[1-(3,5-bis(trifluoromethyl)phenyl)-5-chloro-1,6-dihydro-6-oxopyridazin-4-yl]urea.

One-half gram of 1-(3,5-bis(trifluoromethyl)phenyl)-4-amino-5-chloro-1,6-dihydro-6-oxopyridazine, prepared as in the second paragraph of Example 1, partially dissolved in 50 milliliters of acetonitrile, was treated with 0.6 gram of 2-bromobenzoyl isocyanate at room temperature under a nitrogen atmosphere. The reaction mixture was stirred for about 16 hours. The mixture was cooled in ice and the resulting solid precipitate was removed by filtration. A yield of 0.38 gram (forty-eight percent) of solid product having a melting point of 201°–204° C. was obtained. Nuclear magnetic resonance spectroscopy confirmed that the product was 1-(2-bromobenzoyl)-3-[1-(3,5-bis(trifluoromethyl)phenyl)-5-chloro-1,6-dihydro-6-oxopyridazin-4-yl]urea. Elemental analysis of the product gave the following result:

Calc. for $C_{20}H_{10}BrClF_6N_4O_3$—Theory: C, 41.13; H, 1.71; N, 9.160. Found: C, 40.93; H, 1.82; N, 9.25.

EXAMPLE 3

This example illustrates the synthesis of 1-(2,6-dichlorobenzoyl)-3-[1-(4-chlorophenyl)-1,6-dihydro-6-oxopyridazin-4-yl]urea.

A reaction mixture made up of 8.95 grams of 4-chlorophenylhydrazine hydrochloride, 3.3 grams of potassium hydroxide (85 percent aqueous solution), 14.2 grams of mucobromic acid and 150 milliliters of ethanol was stirred for about 2 hours at a temperature of 25° C. The solvent was evaporated and 40 milliliters of glacial acetic acid and 40 milliliters of acetic anhydride were added. The mixture was then refluxed for about 12 hours. The mixture was permitted to cool which resulted in formation of a precipitate. The precipitate was recovered by filtration and recrystallized from a solvent mixture of ethanol and dimethylformamide. A yield of 12.1 grams of a solid product was obtained. Nuclear magnetic resonance spectroscopy confirmed the structure of the product to be 1-(4-chlorophenyl)-4,6-dibromo-1,6-dihydro-6-oxo-pyridazine.

A solution of 11.0 grams of the pyridazinone intermediate prepared above, 16 milliliters of concentrated ammonium hydroxide and 80 milliliters of dimethyl sulfoxide was placed in a sealed reactor and heated at 110° C. for about 8 hours. A solid precipitated upon cooling and was recovered by filtration to yield 4.3 grams of product. The mother liquor was poured into ice water causing additional product to precipitate. An additional yield of 1.1 grams of solid product was recovered. The product had a melting point of 288°–298° C. Nuclear magnetic resonance spectroscopy confirmed the product to be 1-(4-chlorophenyl)-4-amino-5-bromo-1,6-dihydro-6-oxopyridazine.

This 4-amino-5-bromo compound was hydrogenated to produce 1-(4-chlorophenyl)-4-amino-1,6-dihydro-6-oxopyridazine by partially dissolving 1.5 gram of the compound in 90 milliliters of ethanol. Ten milliliters of 1 N sodium hydroxide and 0.5 gram of palladium on carbon were added and the mixture was reacted in a Parr shaker hydrogenator. When one equivalent of hydrogen had been taken up, the reaction mixture was filtered and the solvent was removed by evaporation.

The solid product was washed with water and recrystallized from a solvent mixture of ethanol and water. The product had a melting point of 230°–235° C. Nuclear magnetic resonance spectroscopy confirmed the product to be 1-(4-chlorophenyl)-4-amino-1,6-dihydro-6-oxopyridazine.

The final product was obtained by partially dissolving 0.2 gram of 1-(4-chlorophenyl)-4-amino-1,6-dihydro-6-oxopyridazine in 30 milliliters of acetonitrile and treating the mixture with 0.3 gram of 2,6-dichlorobenzoyl isocyanate. The reaction mixture was stirred for about 16 hours at room temperature. The solid product which had formed was recovered by filtration and dried. A yield of 0.12 gram of product having a melting point of 236°–270° C. was obtained. Nuclear magnetic resonance spectroscopy confirmed the structure of the product as 1-(2,6-dichlorobenzoyl)-3-[1-(4-chlorophenyl)-1,6-dihydro-6-oxopyridazin-4-yl]urea. Elemental analysis provided the following results:

Calc. for $C_{18}H_{11}Cl_3N_4O_3$—Theory: C, 49.40; H, 2.53; N, 12.80. Found: C, 49,16; H, 2.55; N, 12.61.

EXAMPLE 4

This example illustrates the preparation of 1-(2,6-dichlorobenzoyl)-3-[1-(3-trifluoromethylphenyl)-3-chloro-1,6-dihydro-6-oxopyridazin-4-yl]urea.

A reaction mixture of 7.04 grams of 3-trifluoromethylphenyl hydrazine, 7.03 grams of bromomaleic anhydride and 15 milliliters of acetic acid was refluxed for two hours. The reaction mixture was cooled and permitted to stand for several days during which time it solidified.

The solid was partially dissolved in methylene dichloride and heated. An insoluble solid residue (0.8 grams) was recovered by filtration. This solid material had a melting point of 221°–232° C. Nuclear magnetic resonance spectrum confirmed that this was the desired intermediate, 1-(3-trifluoromethylphenyl)-3-hydroxy-4-bromo-6-pyridazinone. The reaction product that dissolved in the methylene dichloride was separated by chromatography over silica gel into two additional compounds which were identified by NMR and found not to be the desired intermediate.

A mixture of 0.8 gram of 1-(3-trifluoromethylphenyl)-3-hydroxy-4-bromo-6-pyridazinone and 3–4 milliliters of phosphorus oxychloride was refluxed for about 3 hours. The reaction mixture was cooled and poured into ice to cause formation of a precipitate. The precipitate was recovered by filtration. The product had a tendency to gel, a melting point of 68°–71° C., and was not further purified. Nuclear magnetic resonance and infrared spectroscopy confirmed that the product was 1-(3-trifluoromethylphenyl)-3-chloro-4-bromo-6-pyridazinone.

A reaction mixture of 3.2 grams of the 3-chloro-4-bromo compound prepared as described above, 12 milliliters of concentrated ammonium hydroxide and 12 milliliters of water was heated at 100° C. in a sealed tube for 10 hours. The solid precipitate was collected and recrystallized from a solvent system of dichloromethane and petroleum ether. A yield of 1.2 grams of a solid having a melting point of 169°–171° C. was obtained. A nuclear magnetic resonance spectrum was consistent with the desired intermediate, 1-(3-trifluoromethylphenyl)-3-chloro-4-amino-6-pyridazinone.

The final product was prepared by dissolving 0.35 gram of the above intermediate in 20 milliliters of acetonitrile and treating the mixture with 0.45 gram of 2,6-dichlorobenzoyl isocyanate at room temperature under a nitrogen atmosphere. The reaction mixture was stirred for about 16 hours. Some of the solvent was evaporated under reduced pressure causing a precipitate to form. The solid precipitate was recovered by filtration to yield 0.50 gram of solid product having a melting point of 215°–226° C. Nuclear magnetic resonance spectroscopy confirmed the product to be the desired 1-(2,6-dichlorobenzoyl)-3-[1-(3-trifluoromethylphenyl)-3-chloro-1,6-dihydro-6-oxopyridazin-4-yl]urea. Elemental analysis provided the following results:

Calc. for $C_{19}H_{10}Cl_3F_3N_4O_3$—Theory: C, 45.13; H, 1.99; N, 11.08. Found: C, 45.03; H, 2.11; N, 11.08.

EXAMPLE 5

This example illustrates the synthesis of 1-(2,6-dichlorobenzoyl)-3-[1-(3-trifluoromethylphenyl-5-bromo-1,6-dihydro-6-oxopyridazin-4-yl]urea.

A solution of 21.4 grams of mucobromic acid and 13.3 grams of 3-trifluoromethylphenyl hydrazine in 60 milliliters of ethanol was stirred for about 10 minutes. The ethanol was removed by evaporation under reduced pressure, and then 40 milliliters each of glacial acetic acid and acetic anhydride were added to the reaction vessel. The acidic reaction mixture was heated at reflux for 4 hours. The reaction solvent was removed by evaporation under reduced pressure whereupon a solid precipitate formed. The solid was purified by recrystallization from ethanol. A yield of 20.7 grams of 1-(3-trifluoromethylphenyl)-4,5-dibromo-1,6-dihydro-6-oxopyridazine was obtained.

To 20.7 grams of this compound were added 28 milliliters of concentrated ammonium hydroxide and 130 milliliters of dimethyl sulfoxide. The reaction mixture was placed in a sealed tube and heated at 110° C. for 10 hours. The solution was poured into ice water causing a solid precipitate to form. The solid was recovered and then purified by recrystallization from ethanol. A yield of 9.1 grams of a solid having a melting point of 158°–175° C. was obtained. The product consisted essentially of 1-(3-trifluoromethylphenyl)-4-amino-5-bromo-1,6-dihydro-6-oxopyridazine.

A solution of 0.5 gram of this pyridazinone compound partially dissolved in 20 milliliters of 1,2-dichloroethane was prepared. The reaction mixture was treated with 0.5 gram of 2,6-dichlorobenzoyl isocyanate under a nitrogen atmosphere. The solution was stirred at 25° C. for about 3 hours, with all the material being dissolved in about 0.5 hours and remaining in solution thereafter. The solvent was then removed by evaporation under reduced pressure. The solid product obtained was purified by recrystallization from ethanol. A yield of 350 milligrams of a solid having a melting point of 215°–229° C. was obtained. Nuclear magnetic resonance spectroscopy confirmed that the product was 1-(2,6-dichlorobenzoyl)-3-[1-(3-trifluoromethylphenyl)-5-bromo-1,6-dihydro-6-oxopyridazin-4-yl]urea. Elemental analysis provided the following results.

Calc. for $C_{19}H_{10}BrCl_2F_3N_4O_3$—Theory: C, 41.45; H, 1.82; N, 10.18. Found: C, 41.34; H, 2.03; N, 10.08.

EXAMPLE 6

This example illustrates the preparation of 1-(2,6-dichlorobenzoyl)-3-(1-t-butyl-5-chloro-1,6-dihydro-6-oxopyridazin-4-yl)urea.

A solution of 12.4 grams (0.10 mol.) of the hydrochloride salt of t-butyl hydrazine and 6.6 grams of potassium hydroxide (85 percent aqueous solution) and 17.0 gram mucochloric acid dissolved in 300 milliliters of ethanol was prepared. The solution was stirred for 30 minutes at 25° C. The ethanol was removed by evaporation, and then 50 milliliters each of acetic acid and acetic anhydride were added. The mixture was refluxed for about 20 hours. The solid precipitate which formed was removed by filtration while the reaction mixture was still hot. The solution was evaporated under vacuum to yield an oil and a black solid. The solid and oil were purified by chromatography over silica gel using ether as the eluant. A yield of 9.2 grams of a product having a melting point of 48°–54° C. was obtained. Nuclear magnetic resonance spectroscopy and elemental analysis confirmed that the product was 1-t-butyl-4,5-dichloro-1,6-dihydro-6-oxopyridazine.

To 9.0 grams of this product were added 22 milliliters of concentrated ammonium hydroxide and 100 milliliters of dimethyl sulfoxide. The mixture was heated in a sealed reaction vessel at 100° C. for 8 hours. The solution was poured into ice water. The solid which precipitated was recovered and recrystallized from methylene chloride to give 0.9 gram of 1-t-butyl-4-amino-5-chloro-1,6-dihydro-6-oxopyridazine. The product had a melting point of 194°–198° C. and elemental analysis and nuclear magnetic resonance spectroscopy were consistent with the named product.

A solution was prepared by dissolving 0.5 gram of 1-t-butyl-4-amino-5-chloro-1,6-dihydro-6-oxopyridazine, prepared above, in 50 milliliters of ethyl acetate. Then 0.6 gram of 2,6-dichlorobenzoyl isocyanate was added under a nitrogen atmosphere. The reaction mixture was stirred for 18 hours at 24° C. A solid precipitate (370 mg.) was recovered by filtration and dried. The product had a melting point of 251°–255° C. Nuclear magnetic resonance spectroscopy confirmed the structure of the product to be the desired 1-(2,6-dichlorobenzoyl)-3-(1-t-butyl-5-chloro-1,6-dihydro-6-oxopyridazin-4-yl)urea. Elemental analysis of the product gave the following results.

Calc. for $C_{16}H_{15}Cl_3N_4O_3$—Theory: C, 45.99; H, 3.59; N, 13.41. Found: C, 46.49; H, 3.71; N, 13.50.

Numerous additional compounds typical of those encompassed by this invention were prepared using procedures analogous to those detailed above. The following examples are directed to 1-benzoyl-3-(6-oxopyridazin-4-yl)ureas which were synthesized by reaction of the appropriate 2-substituted or 2,6-disubstituted benzoyl isocyanate with the appropriate 4-amino-1,6-dihydro-6-oxopyridazine.

EXAMPLE 7

1-(2,6-Dichlorobenzoyl)-3-[1-(3-trifluoromethylphenyl)-5-chloro-1,6-dihydro-6-oxopyridazin-4-yl]urea
MP 221°–231° C.
Analysis calc. for $C_{19}H_{10}Cl_3F_3N_4O_3$—Theory: C, 45.13; H, 1.99; N, 11.08. Found: C, 44.87 H, 1.95; N, 10.89.

EXAMPLE 8

1-(2-Chlorobenzoyl)-3-[1-(3-trifluoromethylphenyl)-5-chloro-1,6-dihydro-6-oxopyridazin-4-yl]urea
MP 176°–180° C.
Analysis calc. for $C_{19}H_{11}Cl_2F_3N_4O_3$—Theory: C, 48.43; H, 2.35; N, 11.89. Found: C, 48.20; H, 2.46; N, 11.89.

EXAMPLE 9

1-(2-Bromobenzoyl)-3-[1-(3-trifluoromethylphenyl)-5-chloro-1,6-dihydro-6-oxopyridazin-4-yl]urea
MP 197°–201° C.
Analysis calc. for $C_{19}H_{11}BrClF_3N_4O_3$—Theory: C, 44.25; H, 2.15; N, 10.86. Found: C, 44.34; H, 2.18; N, 11.13.

EXAMPLE 10

1-(2-Chlorobenzoyl)-3-[1-(3-trifluoromethylphenyl)-5-bromo-1,6-dihydro-6-oxopyridazin-4-yl]urea
MP 196°–199° C.
Analysis calc. for $C_{19}H_{11}BrClF_3N_4O_3$—Theory: C, 44.25; H, 2.15; N, 10.86. Found: C, 43.98 H, 2.43; N, 11.07.

EXAMPLE 11

1-(2-(Bromobenzoyl)-3-[1-(3-trifluoromethylphenyl)-5-bromo-1,6-dihydro-6-oxopyridazin-4-yl]urea
MP 180°–190° C.
Analysis calc. for $C_{19}H_{11}Br_2F_3N_4O_3$—Theory: C, 40.74; H, 1.98; N, 10.00. Found: C, 40.82; H, 2.21; N, 10.11.

EXAMPLE 12

1-(2,6-Difluorobenzoyl)-3-[1-(3-trifluoromethylphenyl)-5-bromo-1,6-dihydro-6-oxopyridazin-4-yl]urea
MP 214°–219° C.
Analysis calc. for $C_{19}H_{10}BrF_5N_4O_3$—Theory: C, 44.12; H, 1.95; N, 10.83. Found: C, 44.03; H, 2.09; N, 10.68.

EXAMPLE 13

1-(2,6-Dichlorobenzoyl)-3-[1-(3-trifluoromethylphenyl)-1,6-dihydro-6-oxopyridazin-4-yl]urea
MP 201°–203° C.
Analysis calc. for $C_{19}H_{11}Cl_2F_3N_4O_3$—Theory: C, 48.41; H, 2.34; N, 11.89. Found: C, 48.62; H, 2.64; N, 11.85.

EXAMPLE 14

1-(2-Chlorobenzoyl)-3-[1-(3-trifluoromethylphenyl)-1,6-dihydro-6-oxopyridazin-4-yl]urea
MP 193°–196° C.
Analysis calc. for $C_{19}H_{12}ClF_3N_4O_3$—Theory: C, 52.25; H, 2.77; N, 12.83. Found: C, 52.02; H, 2.73; N, 12.91.

EXAMPLE 15

1-(2-Bromobenzoyl)-3-[1-cyclohexyl-5-chloro-1,6-dihydro-6-oxopyridazin-4-yl]urea
MP 237°–242° C.
Analysis calc. for $C_{18}H_{18}BrClN_4O_3$—Theory: C, 47.65; H, 4.00; N, 12.35. Found: C, 47.41; H, 3.90; N, 12.52.

EXAMPLE 16

1-(2-Chlorobenzoyl)-3-[1-cyclohexyl-5-chloro-1,6-dihydro-6-oxopyridazin-4-yl]urea
MP 221°–233° C.
Analysis calc. for $C_{18}H_{18}Cl_2N_4O_3$—Theory: C, 52.81; H, 4.40; N, 13.69 Found: C, 52.56; H, 4.20; N, 13.63.

EXAMPLE 17

1-(2-Bromobenzoyl)-3-[1-(3-trifluoromethylphenyl)-3-chloro-1,6-dihydro-6-oxopyridazin-4-yl]urea MP 235°-238° C.
Analysis calc. for $C_{19}H_{11}BrClF_3N_4O_3$—Theory: C, 44.25; H, 2.15; N, 10.86. Found: C, 43.97; H, 2.32; N, 10.57.

EXAMPLE 18

1-(2,6-Dichlorobenzoyl)-3-[1-(3,5-bis(trifluoromethyl)phenyl)-5-chloro-1,6-dihydro-6-oxopyridazin-4-yl]urea MP 235°-241° C.
Analysis calc. for $C_{20}H_9Cl_3F_6N_4O_3$—Theory: C, 41.87; H, 1.58; N, 9.77. Found: C, 42.13; H, 1.84; N, 10.02.

EXAMPLE 19

1-(2-Chloro-6-fluorobenzoyl)-3-[1-(3,5-bis(trifluoromethyl)phenyl)-5-chloro-1,6-dihydro-6-oxopyridazin-4-yl]urea MP 235°-239° C.
Analysis calc. for $C_{20}H_9Cl_2F_7N_4O_3$—Theory: C, 43.11; H, 1.63; N, 10.06. Found: C, 43.35; H, 1.95; N, 10.23.

EXAMPLE 20

1-(2-Chlorobenzoyl)-3-[1-(3,5-bis(trifluoromethyl)phenyl)-5-bromo-1,6-dihydro-6-oxopyridazin-4-yl]urea
MP 193°-200° C.
Analysis calc. for $C_{20}H_{10}BrClF_6N_4O_3$—Theory: C, 41.16; H, 1.73; N, 9.60. Found: C, 40.92; H, 1.92; N, 9.41.

EXAMPLE 21

1-(2-Chloro-6-fluorobenzoyl)-3-[1-(3,5-bis(trifluoromethyl)phenyl)-5-bromo-1,6-dihydro-6-oxopyridazin-4-yl]urea MP 236°-240° C.
Analysis calc. for $C_{20}H_9BrClF_7N_4O_3$—Theory: C, 39.93; H, 1.51; N, 9.31. Found: C, 39.78; H, 1.80; N, 9.55.

EXAMPLE 22

1-(2-Chlorobenzoyl)-3-[1-(3,5-bis(trifluoromethyl)phenyl)-1,6-dihydro-6-oxopyridazin-4-yl]urea
MP 217°-270° C.
Analysis calc. for $C_{20}H_{11}ClF_6N_4O_3$—Theory: C, 47.59; H, 2.20; N, 11.10. Found: C, 47.65; H, 2.04; N, 10.92.

EXAMPLE 23

1-(2,6-Dichlorobenzoyl)-3-[1-(4-chlorophenyl)-5-chloro-1,6-dihydro-6-oxopyridazin-4-yl]urea
MP 221°-232° C.
Analysis calc. for $C_{18}H_{10}Cl_4N_4O_3$—Theory: C, 45.79; H, 2.14; N, 11.87. Found: C, 45.56; H, 2.25; N, 11.78.

EXAMPLE 24

1-(2-Chlorobenzoyl)-3-[1-(4-chlorophenyl)-5-chloro-1,6-dihydro-6-oxopyridazin-4-yl]urea
MP 218°-221° C.
Analysis calc. for $C_{18}H_{11}Cl_3N_4O_3$—Theory: C, 49.40; H, 2.53; N, 12.80. Found: C, 49.62; H, 2.80; N, 12.62.

EXAMPLE 25

1-(2-Chlorobenzoyl)-3-[1-(4-chlorophenyl)-5-bromo-1,6-dihydro-6-oxopyridazin-4-yl]urea
MP 222°-231° C.

Analysis calc. for $C_{18}H_{11}BrCl_2N_4O_3$—Theory: C, 44.84; H, 2.30; N, 11.62. Found: C, 44.83; H, 2.24; N, 11.66.

EXAMPLE 26

1-(2-Bromobenzoyl)-3-[1-(4-chlorophenyl)-5-chloro-1,6-dihydro-6-oxopyridazin-4-yl]urea
MP 244°-253° C.
Analysis calc. for $C_{18}H_{11}BrCl_2N_4O_3$—Theory: C, 44.84; H, 2.30; N, 11.62. Found: C, 44.71; H, 2.31; N, 11.75.

EXAMPLE 27

1-(2,6-Dichlorobenzoyl)-3-[1-(4-bromophenyl)-5-chloro-1,6-dihydro-6-oxopyridazin-4-yl]urea
MP 228°-236° C.
Analysis calc. for $C_{18}H_{10}BrCl_3N_4O_3$—Theory: C, 41.85; H, 1.95; N, 10.85. Found: C, 42.14; H, 2.13; N, 11.10.

EXAMPLE 28

1-(2-Chlorobenzoyl)-3-[1-(4-bromophenyl)-5-chloro-1,6-dihydro-6-oxopyridazin-4-yl]urea
MP 217°-221° C.
Analysis calc. for $C_{18}H_{11}BrCl_2N_4O_3$—Theory: C, 44.84; H, 2.30; N, 11.62. Found: C, 44.63; H, 2.49; N, 11.36.

EXAMPLE 29

1-(2,6-Dichlorobenzoyl)-3-[1-(3,5-dichlorophenyl)-5-chloro-1,6-dihydro-6-oxopyridazin-4-yl)urea
MP 242°-246° C.
Analysis calc. for $C_{18}H_9Cl_5N_4O_3$—Theory: C, 42.68; H, 1.79; N, 11.06. Found: C, 42.87; H, 1.69; N, 11.21.

EXAMPLE 30

1-(2-Chlorobenzoyl)-3-[1-(3,5-dichlorophenyl)-5-chloro-1,6-dihydro-6-oxopyridazin-4-yl)urea
MP 228°-237° C.
Analysis calc. for $C_{18}H_{10}Cl_4N_4O_3$—Theory: C, 45.79; H, 2.14; N, 11.87. Found: C, 46.01; H, 2.22; N, 11.89.

EXAMPLE 31

1-(2,6-Dichlorobenzoyl)-3-[1-(4-methoxyphenyl)-5-chloro-1,6-dihydro-6-oxopyridazin-4-yl]urea
MP 208°-212° C.
Analysis calc. for $C_{19}H_{13}Cl_3N_4O_4$—Theory: C, 48.79; H, 2.80; N, 11.98. Found: C, 48.58; H, 2.74; N, 12.03.

EXAMPLE 32

1-(2-Chloro-6-fluorobenzoyl)-3-[1-(t-butyl)-5-chloro-1,6-dihydro-6-oxopyridazin-4-yl]urea
MP 199°-209° C.
Analysis calc. for $C_{16}H_{15}Cl_2FN_4O_3$—Theory: C, 47.88; H, 3.74; N, 13.97. Found: C, 47.71; H, 3.45; N, 13.91.

EXAMPLE 33

1-(2,6-Dichlorobenzoyl)-3-[1-(4-methoxyphenyl)-1,6-dihydro-6-oxopyridazin-4-yl]urea
MP 224°-270° C.
Analysis calc. for $C_{19}H_{14}Cl_2N_4O_4$—Theory: C, 52.67; H, 3.26; N, 12.93. Found: C, 52.47; H, 3.12; N, 13.12.

EXAMPLE 34

1-(2,6-Difluorobenzoyl)-3-[1-(t-butyl)-5-chloro-1,6-dihydro-6-oxopyridazin-4-yl]urea

MP 212°–223° C.

Analysis calc. for $C_{16}H_{15}ClF_2N_4O_3$—Theory: C, 49.95; H, 3.93; N, 14.56. Found: C, 49.87; H, 3.72; N, 14.80.

EXAMPLE 35

1-(2-Bromobenzoyl)-3-[1-(t-butyl)-5-chloro-1,6-dihydro-6-oxopyridazin-4-yl]urea

MP 205°–209° C.

Analysis calc. for $C_{16}H_{16}BrClN_4O_3$—Theory: C, 44.93; H, 3.77; N, 13.10. Found: C, 45.21; H, 3.75; N, 12.91.

EXAMPLE 36

1-(2,6-Dichlorobenzoyl)-3-[1-cyclohexyl-5-chloro-1,6-dihydro-6-oxopyridazin-4-yl]urea

MP 243°–249° C.

Analysis calc. for $C_{18}H_{17}Cl_3N_4O_3$—Theory: C, 48.72; H, 3.86; N, 12.63. Found: C, 48.78; H, 3.79; N, 12.75.

EXAMPLE 37

1-(2,6-Dichlorobenzoyl)-3-[1-(4-chlorobenzyl)-5-chloro-1,6-dihydro-6-oxopyridazin-4-yl]urea

MP 235°–248° C.

Analysis calc. for $C_{19}H_{12}Cl_4N_4O_3$—Theory: C, 46.94; H, 2.49; N, 11.53. Found: C, 47.13; H, 2.40; N, 11.33.

EXAMPLE 38

1-(2-Chlorobenzoyl)-3-[1-(4-chlorobenzyl)-5-chloro-1,6-dihydro-6-oxopyridazin-4-yl]urea

MP 298°–201° C.

Analysis calc. for $C_{19}H_{13}Cl_3N_4O_3$—Theory: C, 50.52; H, 2.91; N, 12.40. Found: C, 50.34; H, 2.91; N, 12.25.

EXAMPLE 39

1-(2-Chlorobenzoyl)-3-[1-(t-butyl)-5-chloro-1,6-dihydro-6-oxopyridazin-4-yl]urea

MP 178°–179° C.

Analysis calc. for $C_{16}H_{16}Cl_2N_4O_3$—Theory: C, 50.15; H, 4.21; N, 14.62. Found: C, 50.38; H, 4.24; N, 14.80.

The compounds of this invention are useful for the control of insects of the orders Coleoptera and Lepidoptera. Coleopter includes such insects as Mexican bean beetle, boll weevil, corn rootworm, cereal leaf beetle, flea beetles, borers, Colorada potato beetle, grain beetles, alfalfa weevil, carpet beetle, confused flour beetle, powder post beetle, wireworms, rice weevil, rose beetle, plum curculio, and white grugs. Lepidoptera includes such insects as Southern armyworm, codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm.

A further embodiment of this invention is a method of controlling insects. The method of this invention can be practiced by contacting the insects to be controlled or the locus of the insect infestation with an effective amount of an insecticidal agent of the invention. The novel compounds of this invention can be used as insecticides either directly, or if desired as a formulation in combination with a suitable inert agricultural carrier. Such formulations also are embraced by this invention. The compounds can be mixed with a solid carrier material or dissolved or dispersed in a liquid carrier material. Included in such mixtures, if desired, are adjuvants such as surface-active substances, stabilizers, and related adjuvants commonly employed in insecticidal compositions.

The formulations provided by this invention can take the form of aqueous solutions and dispersions, oil solutions and oil dispersions, pastes, dusts, wettable powders, miscible oils, granules, aerosol preparations and the like. Such formulations will contain from about 1 to about 95 percent by weight of active ingredient admixed with a suitable inert carrier.

The wettable powders, pastes and miscible oils contemplated herein are formulations in concentrated form which are diluted with water or similar diluent before or during use. Wettable powders are a preferred composition for the insecticides of this invention.

The granular preparations of this invention are produced by taking up a 1-benzoyl-3-(6-oxopyridazinyl)-urea in a solvent, after which a granular carrier material such as porous granules, for example pumice or attapulgite clay, mineral non-porous granules such as sand or ground marl, or organic granules, are impregnated with the solution, suitably in the presence of a binder such as a liquosuepte or the like. Such preparations generally contain about 1 to about 15 percent by weight of active ingredient, ideally about 5 percent.

Dust formulations are prepared by intimately mixing an active compound defined by the above formula with an inert solid carrier material in a concentration of, for example, from about 1 to about 50 percent by weight. Examples of suitable solid carrier materials include talc, kaolin, diatomaceous earth, dolomite, gypsum, chalk, bentomite, attapulgite, or mixtures of these and similar substances. It is also possible to use organic carrier materials such as ground walnut shells or the like.

Wettable powder formulations are produced by mixing from about 10 to about 80 parts by weight of a solid inert carrier, such as one of the aforementioned carrier materials, with from about 10 to about 80 parts by weight of the active compound, together with from about 1 to about 5 parts by weight of a dispersing agent such as a ligninsulfonate or alkylnaphthalenesulfonate. Such formulations also contain from about 0.5 to about 5 parts by weight of a wetting agent, such as one of the fatty alcohol sulfates, alkylarylsulfonates, or fatty acid condensation products.

Miscible oil formulations are prepared by dissolving or suspending the active compound in a suitable solvent which is preferably rather immiscible with water, after which an emulsifier is added to the preparation. Suitable solvents include xylene, toluene, high aromatic petroleum distillates, for example solvent naphtha, distilled tar oil, and mixtures of these. Suitable emulsifiers include alkylphenoxypolyglycol ethers, polyoxyethylene sorbitan esters of fatty acids, or polyoxyethylene sorbitol esters of fatty acids. These miscible oils contain the active compound in a concentration of about 2 percent to about 50 percent by weight.

Where an aerosol preparation is desired, such aerosol preparation can be obtained in the usual manner by incorporating the active compound in a solvent which is a volatile liquid suitable for use as a propellant, for example one of the commercially available fluorocarbon propellants.

As is well understood, the preparations containing one of the active compounds of this invention may also include other known pesticidal compounds. This of course broadens the spectrum of activity of the preparation.

The amount of 1-(substituted benzoyl)-3-(substituted-6-oxopyridazinyl)urea which will be insecticidally effective depends upon a variety of factors. Where a given area of plant life is to be protected, such factors include the extent of vegetative surface to be covered, the severity of the insect infestation, the condition of the foilage treated, the temperature, the humidity, etc. In general, however, the application of sufficient formulation to result in an application rate of the active ingredient of about 0.1 to about 1000 ppm. is desirable. A preferred application rate is from about 10 to about 100 ppm.

The insecticidal activity of the novel compounds of this invention has been determined by testing the efficacy of formulations of the compounds against Mexican bean beetle larvae (*Epilachna varivestis*), and against Southern armyworm larvae (*Spodoptera eridania*). These insects are members of the Coleoptera and Lepidoptera orders of insects, respectively. The test procedures are described in detail below.

Test Procedure I

Test formulations were prepared by dissolving 11 milligrams of test compound in 1 milliliter of a solvent-emulsifier system. The solvent-emulsifier system was prepared by adding 5.9 grams of Toximul R and 4.0 grams Toximul S to a mixture of 500 milliliters of acetone and 500 milliliters of ethyl alcohol. (Toximul R and Toximul S are each a sulfonate/nonionic emulsifier blend produced by Stepan Chemical Company, Northfield, Illinois). The solution was then diluted with 10 milliliters of water to provide a solution containing 1000 parts per million (ppm) test compound. One milliliter of this solution was diluted with 9 milliliters of water to provide a formulation having a concentration of 100 parts per million test compound.

The test formulation was sprayed on the leaves of 4- to 6-day old green bean plants. Adequate formulation to wet both tops and bottoms of the leaves was used. Spraying was done with a DeVilbiss special atomizer with a No. 631 cut-off constructed by the DeVilbiss Company, Toledo, Ohio. During the spraying procedure, the nozzle of the atomizer was held 12 to 18 inches from the leaves and was supplied with a pressure of 5-6 pounds per square inch air pressure. The leaves were allowed to dry. Some of the leaves were then removed from the plants and the cut ends wrapped in water-soaked cellucotton. Two treated leaves were placed in a petri dish and five second or third instar Southern armyworm larvae or five second instar Mexican bean beetle larvae were added. Controls using untreated leaves were similarly prepared.

At the end of 4 days the number of dead larvae were counted. From the leaves remaining in the treated and untreated plants, enough leaves to add two additional leaves to each petri dish were removed. Two of these leaves were added to each petri dish, treated or untreated as appropriate. After 3 additional days the final 7 day mortality count was made. In this test each test compound was assigned a rating using the following rating scheme.

| Dead Larvae | % Dead | Rating |
|---|---|---|
| 0 | 0 | 0 |
| 1-2 | 1-50 | 1 |
| 3-4 | 51-99 | 2 |
| 5 | 100 | 3 |

The activity of several compounds of the invention in the test described above are shown in Table I.

TABLE I

| Compound of Example No. | Concen. (ppm) | Mexican Bean Beetle Day 4 | Day 7 | Southern Armyworm Day 4 | Day 7 |
|---|---|---|---|---|---|
| 1 | 1000 | 0 | 3 | 3 | 3 |
|   | 100 | 0 | 3 | 2 | 3 |
| 2 | 1000 | 0 | 2 | 3 | 3 |
|   | 100 | 0 | 1 | 2 | 3 |
| 3 | 1000 | 0 | 1 | 3 | 3 |
|   | 100 | 0 | 0 | 2 | 3 |
| 4 | 1000 | 0 | 2 | 3 | 3 |
|   | 100 | 0 | 1 | 3 | 3 |
| 5 | 1000 | 1 | 1 | 1 | 1 |
|   | 100 | 0 | 0 | 0 | 0 |
| 6 | 1000 | 1 | 2 | 2 | 3 |
|   | 100 | 0 | 1 | 1 | 2 |
| 7 | 1000 | 0 | 0 | 1 | 2 |
|   | 100 | 0 | 0 | 1 | 2 |
| 8 | 1000 | 2 | 3 | 3 | 3 |
|   | 100 | 1 | 3 | 3 | 3 |
| 9 | 1000 | 2 | 3 | 3 | 3 |
|   | 100 | 1 | 3 | 2 | 3 |
| 10 | 1000 | 1 | 2 | 2 | 3 |
|   | 100 | 0 | 0 | 1 | 2 |
| 11 | 1000 | 0 | 2 | 2 | 2 |
|   | 100 | 0 | 0 | 1 | 1 |
| 12 | 1000 | — | — | 1 | 2 |
|   | 100 | — | — | 0 | 1 |
| 13 | 1000 | 2 | 3 | 3 | 3 |
|   | 100 | 1 | 3 | 2 | 3 |
| 14 | 1000 | 1 | 3 | 0 | 0 |
|   | 100 | 0 | 1 | 0 | 0 |
| 15 | 1000 | 0 | 0 | 1 | 1 |
|   | 100 | 0 | 0 | 0 | 0 |
| 16 | 1000 | 0 | 0 | 1 | 2 |
|   | 100 | 0 | 0 | 0 | 0 |
| 17 | 1000 | 0 | 0 | 0 | 2 |
|   | 100 | 0 | 0 | 0 | 0 |
| 18 | 1000 | 1 | 3 | 3 | 3 |
|   | 100 | 0 | 2 | 2 | 3 |
| 19 | 1000 | — | — | 3 | 3 |
|   | 100 | — | — | 3 | 3 |
| 20 | 1000 | 2 | 3 | 3 | 3 |
|   | 100 | 1 | 3 | 3 | 3 |
| 21 | 1000 | — | — | 2 | 3 |
|   | 100 | — | — | 1 | 2 |
| 22 | 1000 | 1 | 1 | 1 | 1 |
|   | 100 | 0 | 0 | 0 | 0 |
| 23 | 1000 | 0 | 0 | 1 | 3 |
|   | 100 | 0 | 0 | 1 | 3 |
| 24 | 1000 | 0 | 0 | 1 | 2 |
|   | 100 | 0 | 0 | 1 | 2 |
| 25 | 1000 | 1 | 1 | 0 | 0 |
|   | 100 | 0 | 0 | 0 | 0 |
| 26 | 1000 | 0 | 0 | 0 | 0 |
|   | 100 | 0 | 0 | 0 | 0 |
|   | 2000 | — | — | 1 | 1 |
| 27 | 1000 | 0 | 0 | 3 | 3 |
|   | 100 | 0 | 0 | 1 | 3 |
| 28 | 1000 | 0 | 0 | 1 | 1 |
|   | 100 | 0 | 0 | 0 | 0 |
| 29 | 1000 | 1 | 1 | 3 | 3 |
|   | 100 | 0 | 0 | 0 | 0 |
| 30 | 1000 | 0 | 2 | 3 | 3 |
|   | 100 | 0 | 0 | 1 | 2 |
| 31 | 1000 | 0 | 0 | 3 | 3 |
|   | 100 | 0 | 0 | 1 | 2 |
| 32 | 1000 | — | — | 3 | 3 |
|   | 100 | — | — | 3 | 3 |

TABLE I-continued

| Compound of Example No. | Concen. (ppm) | Mexican Bean Beetle | | Southern Armyworm | |
|---|---|---|---|---|---|
| | | Day 4 | Day 7 | Day 4 | Day 7 |
| 33 | 1000 | 0 | 0 | 3 | 3 |
| | 100 | 0 | 0 | 1 | 3 |
| 34 | 1000 | — | — | 3 | 3 |
| | 100 | — | — | 3 | 3 |
| 35 | 1000 | 3 | 3 | 3 | 3 |
| | 100 | 2 | 3 | 2 | 3 |
| 36 | 1000 | 0 | 0 | 0 | 0 |
| | 100 | 0 | 0 | 1 | 1 |
| 37 | 1000 | 0 | 0 | 2 | 3 |
| | 100 | 0 | 0 | 1 | 2 |
| 38 | 1000 | 0 | 1 | 2 | 2 |
| | 100 | 0 | 0 | 1 | 1 |
| 39 | 1000 | 3 | 3 | 2 | 2 |
| | 100 | 2 | 2 | 2 | 2 |

Several of the compounds were retested using test formulations containing less than 100 parts per million test compound, as indicated in Table II. The procedure detailed above was followed. From the mortality count the degree of control (percent control) of the larvae population was calculated for each compound and test concentration using the formula:

$$\text{Percent Control} = \frac{A - B}{A} \times 100$$

where
A is the number of larvae surviving in untreated controls; and
B is the number of larvae surviving in treated tests.
The results are reported in Table II.

TABLE II

| Compound of Example No. | Concen. (ppm) | Mexican Bean Beetle | | Southern Armyworm | |
|---|---|---|---|---|---|
| | | Day 4 | Day 7 | Day 4 | Day 7 |
| 1 | 100 | 73 | 100 | 100 | 100 |
| | 50 | 53 | 100 | 100 | 100 |
| | 25 | 47 | 100 | 100 | 100 |
| | 10 | 7 | 20 | 93 | 100 |
| | 10 | — | — | 86 | 100 |
| | 5 | — | — | 47 | 67 |
| | 2.5 | — | — | 13 | 40 |
| | 1.0 | — | — | 0 | 0 |
| 2 | 100 | — | — | 100 | 100 |
| | 50 | — | — | 100 | 100 |
| | 25 | — | — | 100 | 100 |
| | 10 | — | — | 93 | 100 |
| | 10 | — | — | 80 | 100 |
| | 5 | — | — | 47 | 72 |
| | 2.5 | — | — | 27 | 47 |
| | 1.0 | — | — | 33 | 40 |
| | 55 | — | — | 40 | 72 |
| | 10 | — | — | 100 | 100 |
| | 2.5 | — | — | 0 | 47 |
| | 1.0 | — | — | 0 | 0 |
| 3 | 100 | — | — | 100 | 100 |
| | 50 | — | — | 100 | 100 |
| | 25 | — | — | 100 | 100 |
| | 10 | — | — | 47 | 80 |
| | 10 | — | — | 72 | 100 |
| | 5 | — | — | 33 | 72 |
| | 2.5 | — | — | 0 | 27 |
| | 1.0 | — | — | 0 | 7 |
| 4 | 100 | — | — | 60 | 100 |
| | 50 | — | — | 40 | 93 |
| | 25 | — | — | 0 | 27 |
| | 10 | — | — | 5 | 0 |
| | 100 | — | — | 100 | 100 |
| | 50 | — | — | 67 | 87 |
| | 25 | — | — | 60 | 80 |

TABLE II-continued

| Compound of Example No. | Concen. (ppm) | Mexican Bean Beetle | | Southern Armyworm | |
|---|---|---|---|---|---|
| | | Day 4 | Day 7 | Day 4 | Day 7 |
| | 10 | — | — | 0 | 20 |
| 8 | 100 | 80 | 100 | 100 | 100 |
| | 50 | 73 | 100 | 93 | 100 |
| | 25 | 60 | 100 | 60 | 86 |
| | 10 | 7 | 13 | 20 | 27 |
| 9 | 100 | 53 | 100 | 100 | 100 |
| | 50 | 47 | 100 | 100 | 100 |
| | 25 | 40 | 86 | 93 | 100 |
| | 10 | 0 | 27 | 40 | 86 |
| | 10 | — | — | 33 | 80 |
| | 5 | — | — | 0 | 40 |
| | 2.5 | — | — | 0 | 7 |
| | 1.0 | — | — | 0 | 0 |
| 10 | 100 | — | — | 13 | 72 |
| | 50 | — | — | 0 | 0 |
| | 25 | — | — | 0 | 0 |
| | 10 | — | — | 0 | 0 |
| 13 | 100 | 47 | 100 | 100 | 100 |
| | 50 | 27 | 100 | 20 | 100 |
| | 25 | 20 | 100 | 13 | 73 |
| | 10 | 0 | 20 | 7 | 27 |
| 18 | 100 | — | — | 93 | 100 |
| | 50 | — | — | 73 | 100 |
| | 25 | — | — | 40 | 100 |
| | 10 | — | — | 0 | 20 |
| 20 | 100 | 100 | 100 | 100 | 100 |
| | 50 | 47 | 100 | 100 | 100 |
| | 25 | 67 | 100 | 73 | 100 |
| | 10 | 33 | 93 | 0 | 7 |
| | 10 | 86 | 100 | — | — |
| | 5 | 80 | 100 | — | — |
| | 2.5 | 47 | 67 | — | — |
| | 1.0 | 0 | 0 | — | — |
| 23 | 100 | — | — | 40 | 100 |
| | 50 | — | — | 27 | 100 |
| | 25 | — | — | 7 | 73 |
| | 10 | — | — | 0 | 0 |
| 27 | 100 | — | — | 80 | 100 |
| | 50 | — | — | 60 | 100 |
| | 25 | — | — | 20 | 93 |
| | 10 | — | — | 0 | 27 |
| 28 | 100 | — | — | 80 | 100 |
| | 50 | — | — | 60 | 100 |
| | 25 | — | — | 20 | 93 |
| | 10 | — | — | 0 | 27 |
| 30 | 100 | — | — | 100 | 100 |
| | 50 | — | — | 86 | 100 |
| | 25 | — | — | 53 | 93 |
| | 10 | — | — | 47 | 86 |
| | 10 | — | — | 13 | 72 |
| | 5 | — | — | 0 | 60 |
| | 2.5 | — | — | 0 | 20 |
| | 1.0 | — | — | 7 | 7 |
| 35 | 100 | 60 | 93 | 60 | 86 |
| | 50 | 53 | 93 | 13 | 40 |
| | 25 | 13 | 93 | 13 | 13 |
| | 10 | 0 | 86 | 0 | 0 |
| 37 | 100 | — | — | 60 | 100 |
| | 50 | — | — | 20 | 86 |
| | 25 | — | — | 13 | 33 |
| | 10 | — | — | 0 | 0 |
| 39 | 100 | 86 | 93 | — | — |
| | 50 | 72 | 93 | — | — |
| | 25 | 33 | 93 | — | — |
| | 10 | 0 | 40 | — | — |

I claim:
1. A compound having the structural formula:

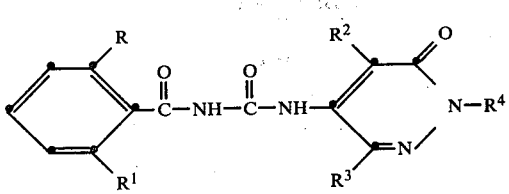

wherein R is chloro, fluoro or bromo, $R^1$ is hydrogen, chloro, fluoro or bromo, $R^2$ and $R^3$ are independently hydrogen, chloro or bromo and $R^4$ is selected from the group consisting of branched alkyl, cycloalkyl, 4-chlorophenyl, 3,5-dichlorophenyl, 4-bromophenyl, 3-trifluoromethylphenyl 3,5-bis(trifluoromethyl)phenyl, 4-chlorobenzyl and 4-methoxyphenyl, with the provisos that when R is fluoro, $R^1$ is other than hydrogen; that one of $R^2$ and $R^3$ is hydrogen; that $R^4$ is other than 3-trifluoromethylphenyl when R is bromo and $R^2$ and $R^3$ are hydrogen, or when R and $R^3$ both are chloro and $R^1$ is hydrogen; and that $R^4$ is 4-methoxyphenyl only when R and $R^1$ both are chloro and $R^2$ is chloro or hydrogen.

2. A compound in accordance with claim 1 wherein $R^4$ is t-butyl, 4-chlorophenyl, 4-bromophenyl, 3,5-dichlorophenyl, 3-trifluoromethylphenyl or 3,5-bis(trifluoromethyl)phenyl.

3. A compound in accordance with claim 2 wherein $R^4$ is 3-trifluoromethylphenyl or 3,5-bis(trifluoromethyl)phenyl.

4. A compound in accordance with claim 1 wherein $R^2$ is chloro or bromo and $R^3$ is hydrogen.

5. A compound in accordance with claim 1 wherein R is chloro, $R^1$ is hydrogen or chloro, $R^2$ is chloro or bromo, $R^3$ is hydrogen and $R^4$ is 3-trifluoromethylphenyl or 3,5-bis(trifluoromethyl)phenyl.

6. A compound in accordance with claim 5 wherein $R^4$ is 3-trifluoromethylphenyl.

7. A compound in accordance with claim 5 wherein $R^4$ is 3,5-bis(trifluoromethyl)phenyl.

8. A compound in accordance with claim 1 wherein R is chloro or fluoro and $R^1$ is hydrogen, chloro or fluoro, with the proviso that when R is fluoro, $R^1$ is other than hydrogen, $R^2$ is chloro, $R^3$ is hydrogen and $R^4$ is t-butyl.

9. A compound in accordance with claim 1 wherein each of R and $R^1$ is chloro, $R^2$ and $R^3$ are independently hydrogen or chloro and $R^4$ is 4-methoxyphenyl.

10. A compound in accordance with claim 1, which compound is 1-(2-chlorobenzoyl)-3-[1-(3,5-bis(trifluoromethyl)phenyl)-5-chloro-1,6-dihydro-6-oxopyridazin-4-yl]urea.

11. A compound in accordance with claim 1, which compound is 1-(2-bromobenzoyl)-3-[1-(3-trifluoromethylphenyl)-5-chloro-1,6-dihydro-6-oxopyridazin-4-yl]urea.

12. A compound in accordance with claim 1, which compound is 1-(2-chlorobenzoyl-3-[1-(3,5-bis(trifluoromethyl)phenyl)-5-bromo-1,6-dihydro-6-oxopyridazin-4-yl]urea.

13. A compound in accordance with claim 1, which compound is 1-(2-chlorobenzoyl)-3-[1-(3,5-dichlorophenyl)-5-chloro-1,6-dihydro-6-oxopyridazin-4-yl]urea.

14. A compound in accordance with claim 1, which compound is 1-(2,6-difluorobenzoyl)-3-[1-t-butyl-5-chloro-1,6-dihydro-6-oxopyridazin-4-yl]urea.

15. A compound in accordance with claim 1, which compound is 1-(2-bromobenzoyl)-3-[1-(3,5-bis(trifluoromethyl)phenyl)-5-chloro-1,6-dihydro-6-oxopyridazin-4-yl]urea.

16. A compound in accordance with claim 1, which compound is 1-(2,6-dichlorobenzoyl)-3-[1-(4-chlorophenyl)-1,6-dihydro-6-oxopyridazin-4-yl]urea.

17. A method of controlling insects of an order selected from Coleoptera and Lepidoptera which comprises applying to the locus of the insect infestation an insecticidally effective amount of a compound of claim 1.

18. A method in accordance with claim 17, wherein said compound is 1-(2-chlorobenzoyl)-3-[1-3,5-(bis(trifluoromethyl)phenyl)-5-chloro-1,6-dihydro-6-oxopyridazin-4-yl]urea.

19. A method in accordance with claim 17, wherein said compound is 1-(2-bromobenzoyl)-3-[1-(3-trifluoromethylphenyl)-5-chloro-1,6-dihydro-6-oxopyridazin-4-yl]urea.

20. A method in accordance with claim 17, wherein said compound is 1-(2-chlorobenzoyl)-3-[1-(3,5-bis(trifluoromethyl)phenyl)-5-bromo-1,6-dihydro-6-oxopyridazin-4-yl]urea.

21. A method in accordance with claim 17, wherein said compound is 1-(2-chlorobenzoyl)-3-[1-(3,5-dichlorophenyl)-5-chloro-1,6-dihydro-6-oxopyridazin-4-yl]urea.

22. A method in accordance with claim 17, wherein said compound is 1-(2,6-difluorobenzoyl)-3-[1-t-butyl-5-chloro-1,6-dihyro-6-oxopyridazin-4-yl]urea.

23. A method in accordance with claim 17, wherein said compound is 1-(2-bromobenzoyl)-3-[1-(3,5-bis(trifluoromethyl)phenyl)-5-chloro-1,6-dihydro-6-oxopyridazin-4-yl]urea.

24. A method in accordance with claim 17, wherein said compound is 1-(2,6-dichlorobenzoyl)-3-[1-(4-chlorophenyl)-1,6-dihydro-6-oxopyridazin-4-yl]urea.

25. An insecticidal formulation comprising about 1 to about 95 percent by weight of a compound of claim 1 admixed with an inert agricultural carrier.

* * * * *